(12) United States Patent
van Veen et al.

(10) Patent No.: US 10,222,339 B2
(45) Date of Patent: Mar. 5, 2019

(54) PH-SENSOR

(75) Inventors: Jacobus Johannes Frederik van Veen, Delft (NL); Cornelis Gerardus Josephus Koopal, Delft (NL)

(73) Assignee: NEDERLANDSE ORGANISATIE VOOR TOEGEPAST-NATUURWETENSCHAPPELIJK ONDERZOEK TNO, Delft (NL)

( * ) Notice: Subject to any disclaimer, the term of this patent is extended or adjusted under 35 U.S.C. 154(b) by 109 days.

(21) Appl. No.: 14/008,256

(22) PCT Filed: Mar. 28, 2012

(86) PCT No.: PCT/NL2012/050200
§ 371 (c)(1),
(2), (4) Date: Dec. 19, 2013

(87) PCT Pub. No.: WO2012/134283
PCT Pub. Date: Oct. 4, 2012

(65) Prior Publication Data
US 2014/0186962 A1 Jul. 3, 2014

(30) Foreign Application Priority Data
Mar. 29, 2011 (EP) ...................................... 11160110

(51) Int. Cl.
*G01N 21/80* (2006.01)
*G01N 21/64* (2006.01)
(Continued)

(52) U.S. Cl.
CPC ............ *G01N 21/80* (2013.01); *G01N 21/643* (2013.01); *G01N 21/645* (2013.01);
(Continued)

(58) Field of Classification Search
CPC ............ G01N 21/643; G01N 21/7702; G01N 31/221; G01N 21/645; G01N 21/7703;
(Continued)

(56) References Cited

U.S. PATENT DOCUMENTS 3,449,080 A 6/1969 Edwards et al.
4,548,907 A 10/1985 Seitz et al.
(Continued)

OTHER PUBLICATIONS

J.W. Attridge, et al., Design of a Fibre-Optic PH Sensor . . . , J. Phys. E. Sci. Instrum., vol. 20, pp. 548-553, 1987.
(Continued)

*Primary Examiner* — Rebecca M Fritchman
(74) *Attorney, Agent, or Firm* — Lucas & Mercanti, LLP

(57) ABSTRACT

The present invention relates to an optical $H^+$-sensor, comprising an $H^+$-indicator material, wherein the $H^+$-indicator material is present between a support material and a H+-permeable layered structure, the layered structure comprising an $H^+$-permeable hydrophilic layer and an $H^+$-permeable cation exchange layer.

Further, the invention relates to a method for determining the $H^+$-concentration, e.g. expressed as pH, in a product or sample thereof, the method comprising contacting the product or sample with an optical $H^+$-sensor according to the invention, measuring an optical property of the indicator material, and determining the $H^+$-concentration of the product or sample based on said optical property.

25 Claims, 2 Drawing Sheets

(51) Int. Cl.
*G01N 21/77* (2006.01)
*G01N 31/22* (2006.01)
*G01N 21/00* (2006.01)

(52) U.S. Cl.
CPC ....... *G01N 21/7703* (2013.01); *G01N 31/221* (2013.01); *G01N 2021/772* (2013.01); *G01N 2021/7786* (2013.01)

(58) Field of Classification Search
CPC ............ G01N 21/80; G01N 2021/772; G01N 2021/7786
USPC ...... 436/20, 22, 163; 422/422, 82.05, 55, 56
See application file for complete search history.

(56) References Cited

U.S. PATENT DOCUMENTS

| | | | | |
|---|---|---|---|---|
| 5,007,989 | A | * | 4/1991 | Nyberg .................. G01N 27/42 204/282 |
| 5,853,669 | A | * | 12/1998 | Wolfbeis .................... 422/82.05 |
| 2007/0270674 | A1 | * | 11/2007 | Kane .................. A61B 5/14546 600/315 |

OTHER PUBLICATIONS

Kevin J. Kuhn, et al., A Renewable-Reagent Fiber . . . , Anal. Chem. vol. 68, pp. 2890-2896, 1996.

* cited by examiner

PH-SENSOR

CROSS-REFERENCE TO RELATED APPLICATIONS

This application is a 371 of PCT/NL2012/050200, filed Mar. 28, 2012, which claims the benefit of European Patent Application No. 11160110.0, filed Mar. 29, 2011, the contents of each of which are incorporated herein by reference.

FIELD OF THE INVENTION

The invention relates to an optical $H^+$-sensor, and to a method of determining the $H^+$-concentration.

BACKGROUND OF THE INVENTION

Optical methods to determine the $H^+$-concentration, e.g. expressed as pH, have been known for many decades. Typically, use is made of a dye of which an optical property (such as extinction at a certain wavelength or fluorescence) changes as it reacts to $H^+$ present in a sample. Thus, the pH of the sample can be indicated. For this reason such dyes are also referred to as pH-indicators or $H^+$ indicators, or in short indicators. Various examples of suitable dyes, together with the pH ranges within which they change colour or another optical property, for instance fluorescence, are generally known in the art, and described in various handbooks, e.g. in "Indicators", E. Bishop, Pergamon Press, 1972, Chapter 3. or 'Haugland, Molecular Probes® Handbook—A Guide to Fluorescent Probes and Labelling Technologies, $11^{th}$ Ed. (2010), e.g. Table 20.1, 20.3 (by Molecular Probes, Inc., Eugene, Oreg., USA) The dye may be added to a liquid of which the pH is to be determined or may be immobilised on a support. In many application the dyes change colour when contacted with a liquid comprising $H^+$, and the colour change can be detected with the naked eye. Alternatively, use can be made of an optical detection system.

U.S. Pat. No. 5,853,669 relates to a sensor membrane for the reversible optical indication of the pH of a sample, having a mechanically stable support element and an indicator dye layer disposed thereon, which comprises a hydrophilic homogeneous, non-fibrous accommodating layer disposed on at least one side of the support element, which layer contains the indicator dye in an immobilized form WO 01/13097 relates to a pH sensor for the visual or optical indication of the pH of a sample, the pH sensor comprising a hydrophilic, intrinsically charged or neutral, synthetic membrane and at least one pH indicator dye immobilized thereto, so as to prevent appreciated bleeding of the at least one indicator from the synthetic membrane upon immersion in an aqueous liquid.

The measurement of the $H^+$-concentration in a sample can be disturbed by various factors, including the potential presence of other dyes in a sample, reactivity of the indicator towards other components in a sample, lipids and salts. This may adversely affect the measurement to a large extent, in particular in case the product of which the $H^+$ concentration is to be determined has a complex composition, as is, e.g. the case for food products for humans, feeds for animals and nutrient products for plants.

SUMMARY OF THE INVENTION

It is an object of the present invention to provide an optical $H^+$-sensor which may serve as an alternative to known $H^+$-sensor or complimentary thereto.

It is in particular an object of the invention to provide a sensor that can also reliably be used for the determination of the $H^+$-concentration in a complex composition, such as a composition comprising one or more components selected from the group of salts, proteins, lipids and carbohydrates.

It is a further object to provide a sensor, which does not demonstrate an unacceptable level of bleeding of indicator material into a product (sample) of which the $H^+$-concentration is determined.

One or more other objects that may be addressed will follow from the description herein below.

It has now been found that one or more of the objects of the invention are met by a sensor wherein an $H^+$-indicator material is situated between specific materials.

Accordingly, the present invention relates to an optical $H^+$-sensor (in particular an optical pH-sensor), comprising an $H^+$-indicator material, wherein the $H^+$-indicator material is present between a support material and a $H^+$-permeable layered structure, the layered structure comprising an $H^+$-permeable hydrophilic layer and an $H^+$-permeable cation exchange layer.

It has been found that such sensor is particularly suitable to determine the $H^+$-concentration in a product, also if the product comprises one or more possibly disturbing components, such as one or more components as mentioned above.

Accordingly, the invention further relates to a method for determining the $H^+$-concentration, e.g. expressed as pH, in a product or sample thereof, the method comprising contacting the product or sample with an optical $H^+$-sensor according to any of the preceding claims, measuring an optical property of the indicator material, and determining the $H^+$-concentration of the product or sample on the basis of said optical property.

It has further been found that the sensor is robust in that it is not or to a low extent adversely affected by the presence of disturbing components as mentioned above.

Further, it has been found that bleeding of an $H^+$ indicator dye is at least substantially avoided in a sensor according to the invention, whilst still allowing the indicator dye to have sufficient mobility in the indicator material layer to be able to react well to pH changes. It is contemplated that the presence of both a hydrophilic layer and cation exchange layer contributes to this advantage.

Further, it has been found that a sensor according to the invention is not only suitable for use at ambient conditions (about 20° C.) or sub-ambient conditions, but may also be used at elevated temperature, such as a temperature above 40° C., e.g. at a temperature in the range of 50-100° C.

Further, in an advantageous embodiment, a sensor according to the invention has one or more advantageous properties selected from selectivity towards $H^+$, dynamic range, accuracy, robustness, detection limit, sensitivity, a reproducibility in terms of repeated measurements with a single sensor (low hysteresis).

DETAILED DESCRIPTION OF THE INVENTION

The selectivity of a sensor is the extent to which the sensor specifically reacts to a change in the $H^+$-concentration, without being affected by a change in other conditions.

The dynamic range of a sensor is the range of a changeable quantity that can be measured with that sensor, the limits of which range are defined by the smallest and the largest value of the changeable quantity that can be measured with that sensor.

The accuracy of a sensor is the closeness of a reading or indication of that detection system to the actual value of the quantity being measured.

Robustness is the extent to which a sensor is resistant to changes in the sensor, influences from a specific sample and influences from the environment. Accordingly, as a sensor is more stable, the back ground noise will be less and/or fewer artefacts will occur in the measuring signal, such a spikes, base line drift and/or base line shifts.

Sensitivity of a sensor is the extent to which the measured signal changes upon a particular change in the concentration or amount of the substance to be detected. The sensitivity is the smallest change in $H^+$-concentration, such as a physical or chemical parameter, that can be detected by the sensor.

The term "or" as used herein means "and/or" unless specified other wise.

The term "a" or "an" as used herein means "at least one" unless specified other wise.

When referring to a 'noun' (e.g. a compound, an additive etc.) in singular, the plural is meant to be included, unless specified otherwise.

The $H^+$-concentration may in particular be measured by measuring an optical property selected from the group of light absorption, extinction, transmission and fluorescence.

The sensor may be operated under alkaline, about neutral or acidic pH. As used herein, the pH is defined as $-\log [H^+]$, wherein $[H^+]$ is the $H^+$-concentration. In particular, especially for an aqueous system, the pH may be in the range of about 2 to about 10, more in particular in the range of about 3 to about 9. In particular good results have been achieved with a sensor for measuring at an acidic pH, in particular in an aqueous liquid, more in particular in an aqueous liquid having a pH of about 3 to about 6. This range, and in particular the range of pH 3.5 to pH 4.5, is amongst others important for various food application.

In particular a sensor for measuring a pH in the range of pH 3 to pH 6 may comprise one or more indicator dyes selected from the group of indicators selected from the group of porphyrines and phorphynes. Such a sensor may amongst others be used for a pH measurement in a food application, e.g. before, during or after pasteurisation of the food. The term food is used herein broadly for products that are nutritional; the term food includes beverages.

In a further embodiment, the sensor is for measuring at a pH in the range of about 5 to about 10.

Preferably, the product or sample thereof comprises a liquid phase. Examples thereof are slurries, suspensions, dispersions and liquids (solvents). Preferably, liquid phase is aqueous, although the liquid phase may be another protic solvent or mixture of other protic solvents. Aqueous liquids comprise water as the only or major liquid component, typically 50-100 wt. %, preferably 80-100 wt. %, more preferably 95-100 wt. %. Other liquids that may be present include alcohols, in particular ethanol, glycerol, and triglyceride oils.

In a preferred embodiment, a sensor according to the invention is for determining the $H^+$-concentration in a food product, in particular a food product selected from the group of sauces, soups, dairy products, dairy substitute products.

In a further embodiment, a sensor according to the invention is for determining the $H^+$-concentration in a nutrient substrate for growing a plant, in particular a nutrient substrate used in a greenhouse wherein plants are grown.

Further, a sensor according to the invention may be used in the chemical process industry for determining the $H^+$-concentration, e.g., in a chemical process stream.

Further, a sensor according to the invention may be used for determining the $H^+$-concentration in water or an aqueous liquid. The sensor may in particular be used for determining the $H^+$-concentration in the production of tap water or it may be used for determining the $H^+$-concentration in water in or from a body of water, such as a canal, a river, lake or sea.

A sensor according to the present invention may be used off-line or in an in-line measurement. In-line measurement is a measurement in a process-line wherein the product of which the $H^+$-concentration is to be tested is manufactured, further processed or used. For example in food/feed/pharmaceutical application, examples of further processing wherein the sensor in particular may be used include heat-treatments (pasteurisation/sterilisation), packaging (canning).

In a basic form, the sensor may consist of $H^+$-indicator material, support material and the $H^+$-permeable layered structure. In such form, a change in concentration may be observed with the naked eye (as with the classical 'pH-indicator papers'). FIG. 1 schematically shows an arrangement of materials in a sensor according to the invention. Support material 1—preferably a wave guide, such as an optical fibre—supports the indicator material 2 (usually hydrophilic and comprising an indicator dye). Indicator material 2 is covered by a cation exchange layer 3, which in turn is covered by a hydrophilic layer 4. The hydrophilic layer is—during use—in contact with a product (sample) of which the $H^+$-concentration (pH) is to be determined. The sensor may be provided with a sample holder 5 or a flow through cell for product(sample) of which the $H^+$-concentration (pH) is to be determined, which is adapted to bring the product(sample) into contact with the hydrophilic layer 4, such that $H^+$ can migrate (diffuse) through hydrophilic layer 4 and cation exchange layer 3 into indicator material 2.

FIG. 2 shows an embodiment wherein the support material 2 is an optical fibre, at the end or which indicator material 2, cation exchange layer 3, and hydrophilic layer 4 are provided. Via the fibre incoming light ($\lambda_{ex1}$, $\lambda_{ex2}$), which in case of a fluorescence-based sensor comprises light with a suitable excitation wavelength can be guided to the indicator material and returning light ($\lambda_{em}$), which in case of a fluorescence-based sensor comprises light at an emission wavelength of the fluorescent dye comprised in the indicator material can be guided from the indicator material (usually to a detector, not shown).

In principle a sensor may be adapted to be read-out by the naked eye. However, for more accurate results, improved sensitivity and improved detectibility, the optical sensor is preferably operated with a light-source and a photodetector. Accordingly, the optical $H^+$-sensor preferably comprises a light-source and a photodetector which light-source and photodetector are—at least during use—in optical communication with the $H^+$-indicator material. The light source and photo-detector may in principle be any light source and detector suitable to generate respectively detect light of a wavelength suitable for use with the indicator(s) in the sensor. For example the light source may be selected from LED's, deuterium lamps, halogen lamps and LASERS. The photodetector may in particular be a photodiode, although e.g. a CCD camera or photon multiplier tube is a suitable alternative.

The sensor may further be provided with electronics to operate the sensor, such as to regulate the light source, to register the output of the photodetector and/or to transform the detector-output into an $H^+$-concentration, e.g. presented as pH-value. Further, the sensor may be provided with one or more optical filters. Such filters are generally known in the art.

The support can in principle be chosen from any support that is suitable for use in an optical $H^+$-sensor in a specific application. In a preferred embodiment, the support is polymeric. Such a sensor is advantageous in particular in food applications, since the sensor can thus be free of glass, which is desired or even a legal requirement for food processing, in order to avoid the risk of contamination of the product with pieces of glass Advantageously, the support material is a waveguide, in particular a polymeric waveguide. Thus, the sensor can be read out at a distance.

In particular for fluorescence-based sensors, it is possible to provide a sensor of which the read-out can also be read out through the air. For instance, the indicator material, cation exchange layer and hydrophilic layer can be provided inside a container (e.g. a food packaging) which acts as the support material. A detector can then be positioned on the outside. This is what is called non-invasive detection and this is also one of the preferred embodiments for the pH sensor. In particular if at least the part of the container where the indicator material, cation exchange layer and hydrophilic layer are provided, is transparent, a change in pH may be observed by the naked eye as the pH-dependent optical property of the indicator material changes.

For the purpose of the invention, the term 'waveguide' is used for optical waveguides. An optical waveguide is a physical structure that guides electromagnetic waves in at least part of the optical spectrum, i.e. in at least part of the spectrum formed by the infrared, visible and ultraviolet ranges of the electromagnetic spectrum. In general, a waveguide is of elongate form. Common types of waveguides include optical fibres, e.g. as referred to in the above cited prior art, and rectangular waveguides. Waveguides are commercially obtainable from various sources.

In an advantageous embodiment, the optical $H^+$-sensor according to claim 2, wherein the waveguide is an optical fibre. In particular, good results have been achieved with a sensor wherein the $H^+$-indicator material and $H^+$-permeable layered structure is provided at the base (tip) of the fibre. Although, in principle it may also be provided at a part of the curved surface.

The $H^+$-permeable hydrophilic layer typically is more permeable to ions like $H^+$- (including its hydrated forms such as $H_3O^+$) and other inorganic ions such as halogen ions, alkaline (earth) metal ions and the like than to lipids, such as glycerides or fatty acids. Preferably it is essentially impermeable to lipids. The skilled person will be able to choose a suitable material for the hydrophilic layer, based on common general knowledge, the information disclosed herein and optionally a limited amount of routine testing. In particular, a suitable hydrophilic material may have a solubility for NaCl of at least 5 wt. %, preferably at least. 10 wt. %, at ambient temperature (20° C.).

Particularly suitable as a $H^+$-permeable hydrophilic layer is a material selected from the group of hydrogels and ionomers. Preferably the layer is a hydrogel.

In a specific embodiment, the hydrophilic layer, in particular a hydrogel, comprises a polymer selected from polyacrylates and polymethacrylates, including copolymers thereof.

The poly(meth)acrylate may be derivatised. A preferred poly(meth)acrylate derivative is polyHydroxyEthylMethacrylate (polyHEMA). In particular, the hydrophilic layer may be a hydrogel comprising polyHEMA.

In a further specific embodiment, the hydrophilic layer, in particular a hydrogel, comprises a polymer selected from the group of polyvinylalcohols, polysugars, polysugar alcohols, polylactate, including copolymers and derivatives thereof.

The hydrophilic outer layer usually has a thickness in the range of 50 to 1000 µm. A thickness of at least 50 µm, in particular of at least 100 µm is in particular preferred for a good mechanical integrity. A thickness of 500 µm or less, in particular of 200 µm or less is in particular preferred for a fast response time The $H^+$-permeable cation exchange layer is in general essentially non-permeable for ions other than $H^+$, including its hydrated forms, and other inorganic cations (such as metal ions).

The $H^+$-permeable cation exchange layer may in particular be made form any cation exchange material that allows permeation of $H^+$. In particular, good results have been achieved with a sulphonated polymeric cation exchange material, more in particular a sulphonated fluoropolymer, such as nafion.

The cation exchange layer usually has a thickness in the range of 1 µm to 100 µm. A thickness of at least 2 µm, in particular of at least 5 µm is in particular preferred for good mechanical integrity. A thickness of 20 µm or less, in particular of 10 µm or less is in particular preferred for a fast response time.

The $H^+$-indicator material may be based on indicators and supports for the indicator known in the art. It may e.g. comprise an indicator and/or support mentioned in the above cited prior art. Preferably, it comprises a $H^+$-indicator dye selected from the group of fluorescent $H^+$-indicators. These fluorescent $H^+$-indicators may amongst others be selected from those described in the above identified prior art.

The main consideration for a useful fluorescent pH indicator is that the fluorescence intensity of the compound be correlated as reliably as possible with the pH of the medium being measured. An extensive list of readily available fluorescent pH indicators covering the pH range 0 to 14 has been published by G. G. Guilbault in "Practical Fluorescence" (1973).

Many of the fluorescent pH indicators known in the art are phenolic derivatives that undergo absorption shifts to longer wavelength in basic solution, usually with an accompanying increase in fluorescence intensity. Since these rely on deprotonation of a phenol-type functionality to enhance fluorescence intensity, they exhibit a decrease in fluorescence intensity with increasing acidity at longer emission wavelengths. Fluorescein and the umbelliferones are examples of this type of indicator (R. P. Haugland. 1989. "Molecular Probes Handbook" from Molecular Probes, Inc. , Eugene, Oreg., pg. 30, FIGS. 4.2 and 4.3).

Seminaphthorhodafluor (SNARF) and seminaphthofluorescein (SNAFL) pH indicators have been developed which are useful for measuring pH changes in the range of about 6.3 to 8.

2', 7'-bis-(2-carboxyethyl)-5-(and-6) carboxyfluorescein, (BCECF) is a pH sensitive dye with a side group linked to the fluorescein moiety which consists of two one-carbon spacers attached to carboxylic acids. R. P. Haugland, 1989, supra, pg. 88 and 93, compound B-1151.

In particular, a fluorescent $H^+$-indicator may be selected from the group of porphyrines, porphynes, (carboxy)fluoresceins, pyranines, and xanthenes.

Further suitable Htindicators are described in U.S. Pat. No. 5,302,731.

In a preferred embodiment, the $H^+$-indicator material comprises a $H^+$-indicator dye coupled to a hydrophilic polymer. The coupling may be accomplished in a manner known per se, depending on the functional groups the polymer and the indicator dye. For instance, dye and polymer can be coupled via an ester linkage if one comprises a hydroxyl functionality and the other a carboxylic acid functionality or via peptide linkage if one comprises an amine and the other a carboxylic acid functionality.

A suitable concentration for the indicator dye may be determined empirically, depending on the intended purpose and the chosen materials. The skilled person will be able to do this based on the information disclosed herein, the cited prior art and common general knowledge. Usually a suitable concentration is chosen in the range of 0.1-10 wt. %, in particular in the range of 0.5 to 5 wt. %.

In an advantageous embodiment, the $H^+$-indicator material comprises light-reflecting particles. This is in particular advantageous for a sensor making use of fluorescence detection. The reflecting particles can enhance fluorescence intensity. The reflecting particles may in particular contribute to improved sensitivity and/or an improved limit of detection. Also it may contribute to a shielding of incoming light from the surroundings of the sensor, which could increase noise signal.

The reflecting particles are preferably nanoparticles or microparticles, in particular nanoparticles having an average diameter in the range of 20 to 500 nm or microparticles having an average diameter in the range of 1 to 50 μm. Examples of reflecting particles are latex-particles, glass particles, quartz particles, silicagel. In particular good results have been achieved with microparticles of controlled pore glass (CPG) for improved sensitivity. Such particles are commercially available e.g. from Millipore or Sigma-Aldrich.

The invention will now be illustrated by the following example.

EXAMPLE

Optical (Fluorescent) pH Sensor for Food Applications (Pasteurisation)

The sensor had a design as schematically shown in FIG. 2. It consisted of a pH sensitive, fluorescent coating, consisting of a three layer system. The first layer positioned on the distal end of the polymer fibre 1 (3 mm diameter) was the indicator material 2 and consisted of a mixture of silicagel and the indicator MCP (meso-Tetra(4-carboxyphenyl) porphyrine) that was covalently coupled to PVP-$NH_2$ (poly[N-ethylamine-(4-vinyl)pyridine]), in an amount of about 24 mol MCP per mol PVP. It had a thickness of abut 5 μm. The second layer was a layer of Nafion (cation exchange material 3), which was applied by casting of a 5% alcoholic solution of the Nafion on top of the first layer. The third layer was the hydrophilic layer 3 and consisted of polyvinylalcohol, applied by casting of a solution of a polyvinylalcohol solution (10%) with glutaraldehyde (0.5%) and acid (HCl, 70 mM) for in-situ crosslinking.

Figure 1:
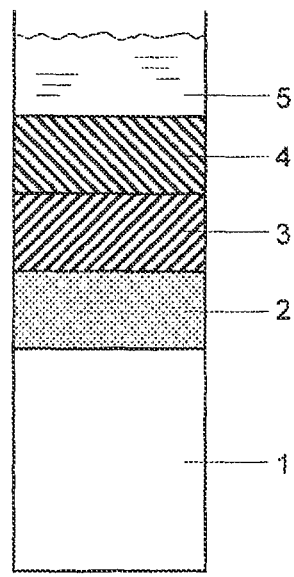
Figure 2:
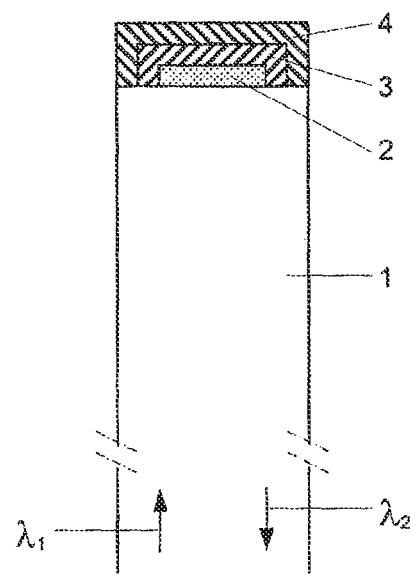
Figure 3:
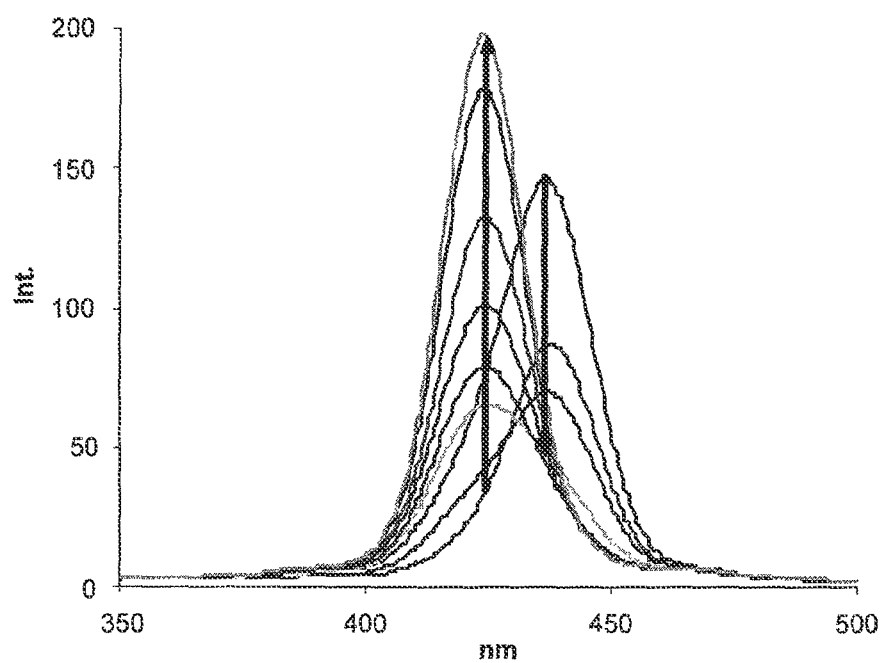
FIG. 3 shows a measurement of the fluorescent intensity at two excitation wavelengths, a so-called excitation-ratio measurement.
Figure 4:
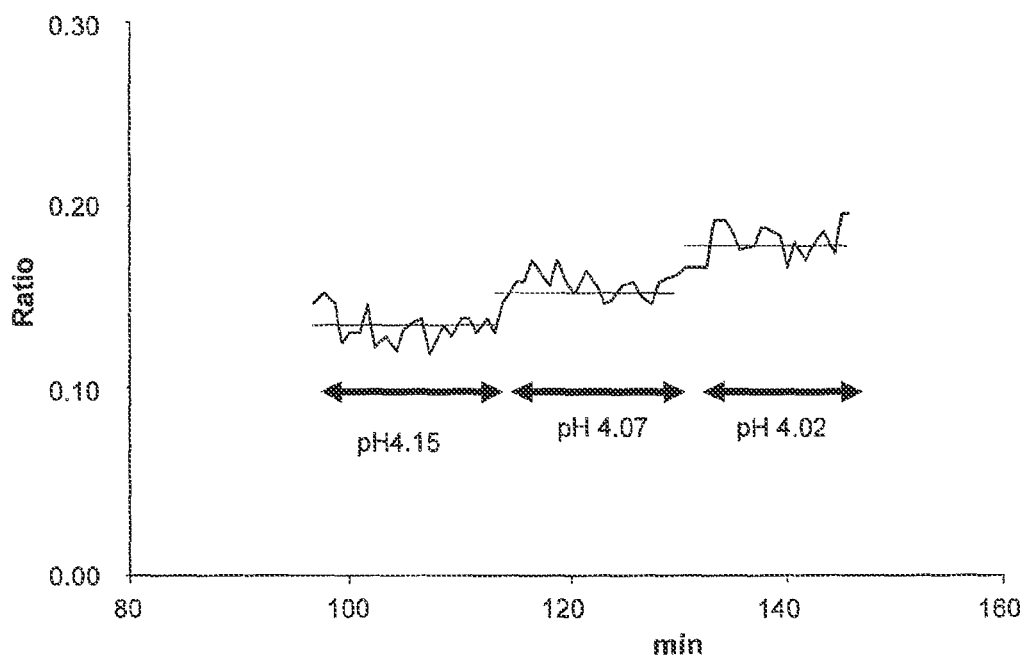
FIG. 4 shows an example of an in-line measurement with the opticalpH sensor in a sauce at elevated temperature (65° C.)

The invention claimed is:

1. Optical $H^+$-sensor, comprising an $H^+$-indicator material, wherein:
the $H^+$-indicator material comprises a $H^+$-indicator dye covalently coupled to a hydrophilic polymer,
the $H^+$-indicator material being situated between a support material and an $H^+$-permeable layered structure,
the $H^+$-permeable layered structure comprising an $H^+$-permeable hydrophilic layer and an $H^+$-permeable cation exchange layer, and
the $H^+$-permeable cation exchange layer being situated between the $H^+$-indicator material and the $H^+$-permeable hydrophilic layer.

2. Optical $H^+$-sensor according to claim 1, wherein the support material is a waveguide, in particular a polymeric waveguide.

3. Optical $H^+$-sensor according to claim 2, wherein the waveguide is an optical fibre.

4. Optical $H^+$-sensor according to claim 1, wherein the $H^+$-permeable hydrophilic layer is selected from the group consisting of hydro-gels and ionomers.

5. Optical $H^+$-sensor according to claim 1, wherein the $H^+$-permeable hydrophilic layer comprises a polymer selected from the group consisting of poly(meth)acrylates, polyvinylalcohols, polysugars, polysugar alcohols and polylactates, including copolymers and derivatives thereof.

6. Optical $H^+$-sensor according to claim 1, wherein the $H^+$-permeable cation exchange layer is selected from the group consisting of sulphonated cation exchange materials.

7. Optical $H^+$-sensor according to claim 1, wherein the $H^+$-indicator material comprises an $H^+$-indicator dye selected from the group consisting of fluorescent $H^+$-indicators.

8. Optical $H^+$-sensor according to claim 1, wherein the $H^+$-indicator material comprises reflecting particles.

9. Optical $H^+$-sensor according to claim 1, wherein the sensor comprises a light-source and a photo-detector which light-source and photodetector are—at least during use—in optical communication with the $H^+$-indicator material.

10. Method for determining the $H^+$-concentration, in a product or sample thereof, the method comprising contacting the product or sample with an optical $H^+$-sensor according to claim 1, measuring an optical property of the $H^+$-indicator material, and determining the $H^+$-concentration of the product or sample based on said optical property.

11. Method according to claim 10, wherein the $H^+$-concentration is determined in-line in a process for manufacturing or further processing the product.

12. Method according to claim 10, wherein the product is a food product.

13. Method according to claim 10, wherein the product or sample thereof has a pH in the range of 3-10.

14. A method for determining the $H^+$-concentration in water or an aqueous liquid, comprising contacting a sample of water or an aqueous liquid with an optical $H^-$-sensor comprising an $H^+$-indicator material, wherein:
the $H^+$-indicator material comprises a $H^+$-indicator dye covalently coupled to a hydrophilic polymer,
the $H^+$-indicator material being situated between a support material and an $H^+$-permeable layered structure,
the $H^+$-permeable layered structure comprising an $H^+$-permeable hydrophilic layer and an $H^+$-permeable cation exchange layer, and
the $H^+$-permeable cation exchange layer being situated between the $H^+$-indicator material and the $H^+$-permeable hydrophilic layer.

15. Optical $H^+$ sensor according to claim 1, wherein the $H^-$-permeable cation exchange material is a sulphonated fluoropolymer.

16. Optical H+ sensor according to claim 15, wherein the sulphonated fluoropolymer is a nafion.

17. Optical H+-sensor according to claim 7, wherein the fluorescent H+-indicator is selected from the group consisting of porphyrines, porphynes, carboxy-fluoresceins, pyranines and xanthenes.

18. Optical H+-sensor according to claim 8, wherein the reflecting particles are selected from the group consisting of glass particles and silicagels.

19. Method according to claim 12, wherein the food product is selected from the group of sauces, soups, dairy products, and dairy substitute products.

20. Method according to claim 10, wherein the product is a nutrient substrate for growing a plant.

21. Method according to claim 20, wherein the nutrient substrate is used in a greenhouse wherein plants are grown.

22. Method according to claim 10, wherein the product is a chemical product.

23. Method according to claim 13, wherein the product or sample thereof has a pH in the range of 3-6.

24. Method according to claim 13, wherein the product or sample thereof has a pH in the range of 5-10.

25. Optical H+-sensor according to claim 1, wherein the H+-indicator dye is covalently coupled to the H+-permeable hydrophilic polymer via an ester linkage or a peptide linkage.

* * * * *